United States Patent [19]

Bracken et al.

[11] Patent Number: 5,539,020

[45] Date of Patent: Jul. 23, 1996

[54] METHOD AND DEVICE FOR CUSHIONING LIMBS

[75] Inventors: Ronald L. Bracken, Memphis, Tenn.; Ralph A. Winn, Santa Barbara; Norman L. Riley, Ojai, both of Calif.

[73] Assignee: Schering-Plough HealthCare Products, Inc., Memphis, Tenn.

[21] Appl. No.: 356,295

[22] PCT Filed: Jul. 1, 1993

[86] PCT No.: PCT/US93/06111

§ 371 Date: Dec. 19, 1994

§ 102(e) Date: Dec. 19, 1994

[87] PCT Pub. No.: WO94/01496

PCT Pub. Date: Jan. 20, 1994

Related U.S. Application Data

[63] Continuation-in-part of Ser. No. 28,925, Mar. 4, 1993, abandoned, which is a continuation of Ser. No. 932,422, Aug. 19, 1992, abandoned, which is a continuation-in-part of Ser. No. 909,360, Jul. 6, 1992, abandoned, and Ser. No. 909,361, Jul. 6, 1992, abandoned.

[51] Int. Cl.$^6$ ..................................................... C08G 77/12
[52] U.S. Cl. ........................... 523/212; 524/862; 528/15; 528/31; 528/32; 128/889; 128/892; 128/893; 128/894
[58] Field of Search ................................. 528/15, 31, 32; 524/862; 527/212; 128/889, 892, 893, 894

[56] References Cited

U.S. PATENT DOCUMENTS

| | | |
|---|---|---|
| 1,001,161 | 8/1911 | Packard . |
| 1,080,303 | 12/1913 | Scholl . |
| 1,580,170 | 4/1926 | Scholl . |
| 2,556,887 | 6/1951 | Ryan . |
| 2,641,066 | 6/1953 | Filardo . |
| 3,186,006 | 6/1965 | Miller . |
| 3,213,048 | 10/1965 | Boot . |
| 3,220,972 | 11/1965 | Lamoreaux . |
| 3,247,845 | 4/1966 | Kennedy . |
| 3,253,600 | 5/1966 | Scholl . |
| 3,253,601 | 5/1966 | Scholl . |
| 3,445,420 | 5/1969 | Kookootsedes et al. . |
| 3,548,420 | 12/1970 | Spence . |
| 3,594,813 | 7/1971 | Sanderson . |
| 3,635,743 | 1/1972 | Smith . |
| 3,663,973 | 5/1972 | Spence . |
| 3,692,023 | 9/1972 | Philips et al. . |
| 3,723,497 | 3/1973 | Baney . |
| 3,839,246 | 10/1974 | Hamilton, Jr. et al. . |
| 3,862,869 | 1/1975 | Peterson et al. . |
| 3,880,155 | 4/1975 | Rosoff . |
| 3,884,866 | 5/1975 | Jeram et al. . |
| 4,019,209 | 4/1977 | Spence . |
| 4,061,609 | 12/1977 | Bobear . |
| 4,101,499 | 7/1978 | Herzig . |
| 4,162,243 | 7/1979 | Lee et al. . |
| 4,189,546 | 2/1980 | Deichert et al. . |
| 4,322,320 | 3/1982 | Caprino . |
| 4,332,844 | 6/1982 | Hamada et al. . |
| 4,413,359 | 11/1983 | Akiyama et al. . |
| 4,460,739 | 7/1984 | Ashby . |
| 4,573,216 | 3/1986 | Wortberg . |
| 4,601,286 | 7/1986 | Kaufman . |
| 4,623,593 | 11/1986 | Baier et al. . |
| 4,655,210 | 4/1987 | Edenbaum et al. . |
| 4,660,553 | 4/1987 | Naylor et al. . |
| 4,699,134 | 10/1987 | Samuelson . |
| 4,743,499 | 5/1988 | Volke . |
| 4,803,078 | 2/1989 | Sakai . |
| 4,856,502 | 8/1989 | Ersfeld et al. . |
| 4,950,291 | 8/1990 | Mulligan . |
| 4,960,116 | 10/1990 | Milner . |
| 5,063,063 | 11/1991 | Miller . |
| 5,103,812 | 4/1992 | Salamone et al. . |
| 5,112,640 | 5/1992 | Warunek et al. . |
| 5,114,794 | 5/1992 | Sudo et al. . |
| 5,156,601 | 10/1992 | Lorenz et al. . |

FOREIGN PATENT DOCUMENTS

| | | |
|---|---|---|
| 0091737A3 | 10/1983 | European Pat. Off. . |
| 0489518A1 | 10/1992 | European Pat. Off. . |
| 2225480 | 11/1974 | France . |
| 2620933-A | 3/1989 | France . |
| 2660168 | 10/1991 | France . |

OTHER PUBLICATIONS

American Society For Testing and Materials (ASTM) Designation: D2979–71 (Reapproved 1982), Standard Test Method for Pressure–Sensitive Tack of Adhesives Using an Inverted Probe Machine, pp. 187–189, from the Annual Book of ASTM Standards, vol. 15.09.

Tack Rolling Ball: Test Methods for Pressure Sensitive Tapes, 9th Edition, PSTC–6, revised Aug., 1989, pp. 29–30.

ASTM Designation:E96–80, Standard Test Methods for Water Vapor Transmission of Materials, edited May 197, pp. 629–633.

*Primary Examiner*—Ralph H. Dean
*Attorney, Agent, or Firm*—Joseph T. Majka; Robert A. Franks

[57] ABSTRACT

A soft, tacky polysiloxane elastomer characterized as having: a tackiness of 10–450 grams as determined by a polyken probe tack tester or 0–10 cm (0–4 inches) as determined by a rolling ball tack tester and a tensile strength of 0.14–5.52 mega Pascals (20–800 pounds/square inch), a minimum elongation of 250–1100 percent and a tear strength of 0.88–35.2 kN/m (5–200 pound/square inch) The soft, tacky elastomer can be made into various cushioning devices, with or without a topcover. Representative cushioning devices include an arch support pad, a metatarsal pad, a heel cushion, sheet padding, a full-length insole, a three quarter length insole, a half insole, a toe-crest pad, a heel liner, an elbow pad, a corn pad, a callus pad, a blister pad, a bunion pad or a toe pad.

19 Claims, 6 Drawing Sheets

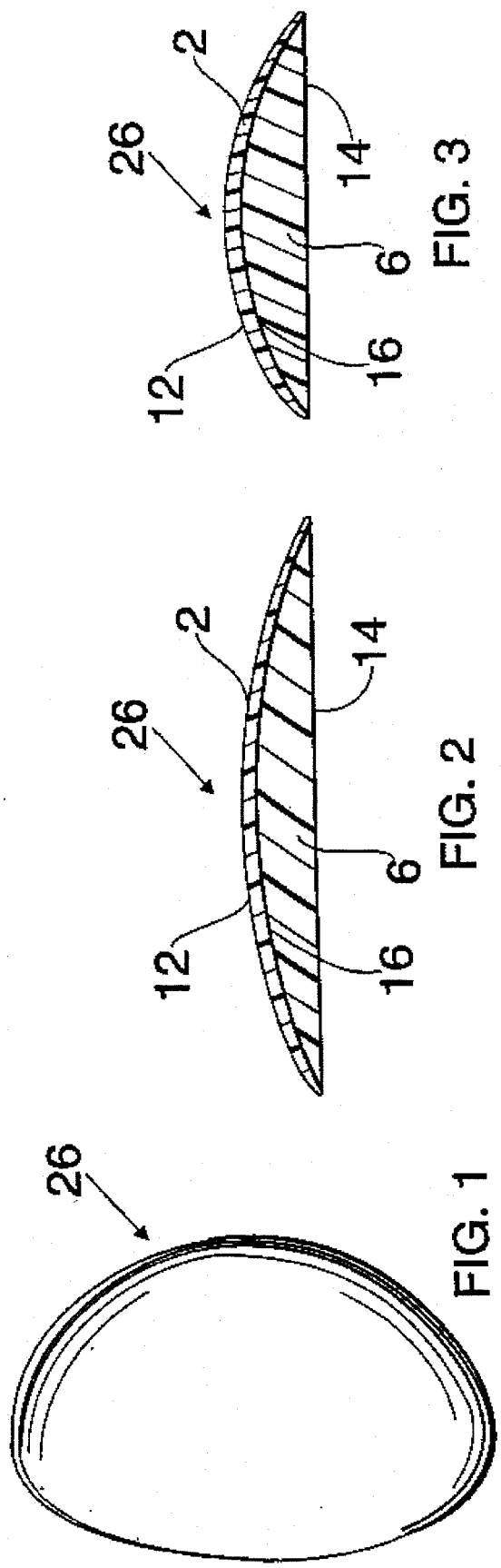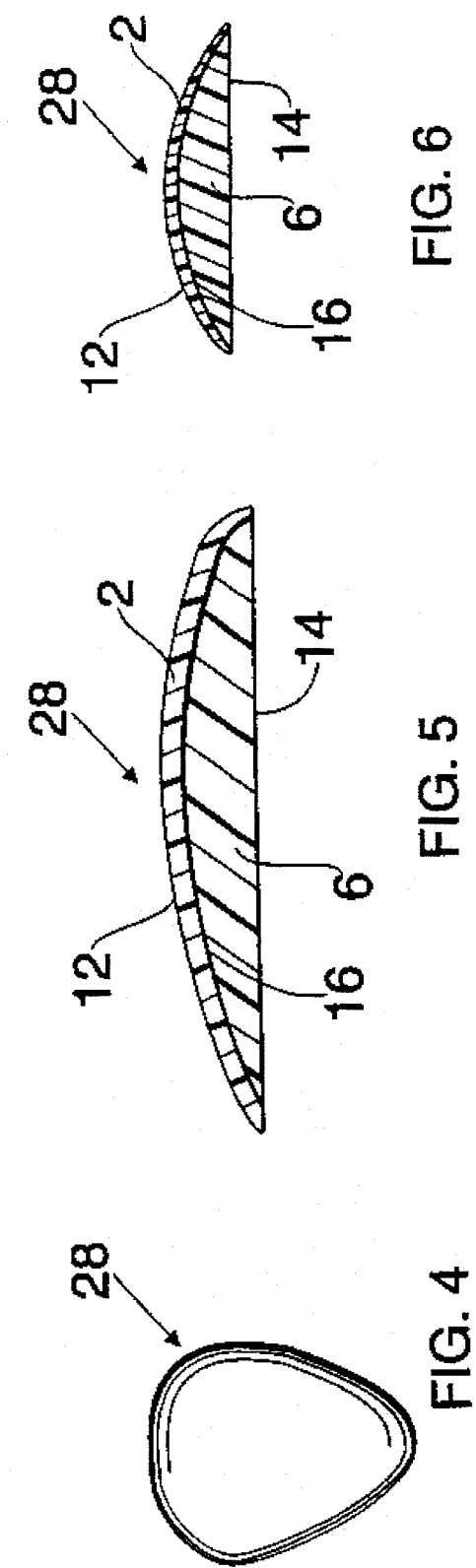

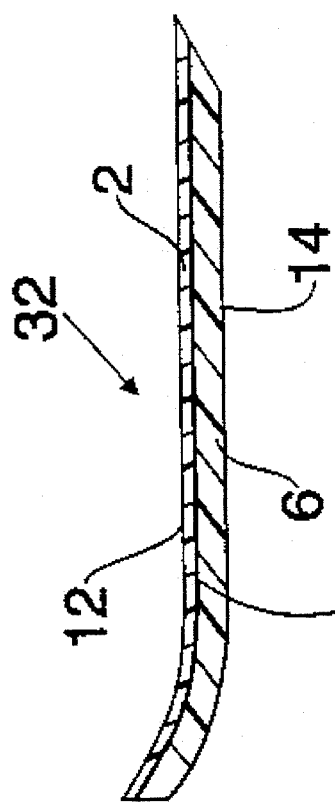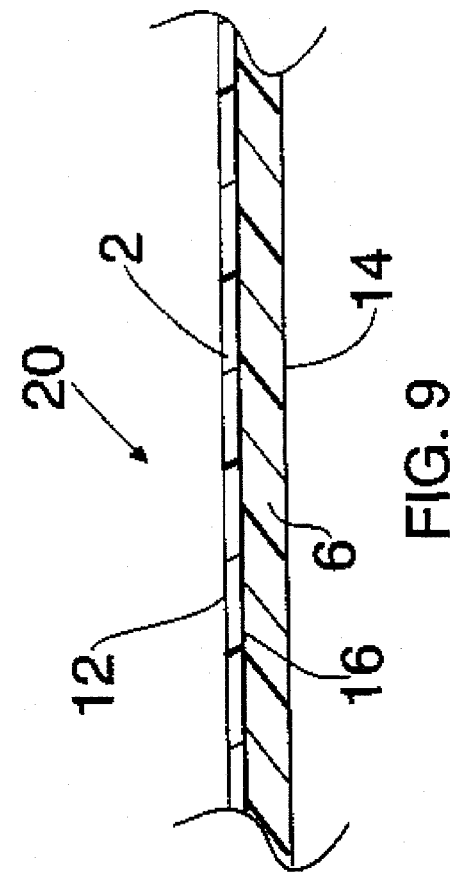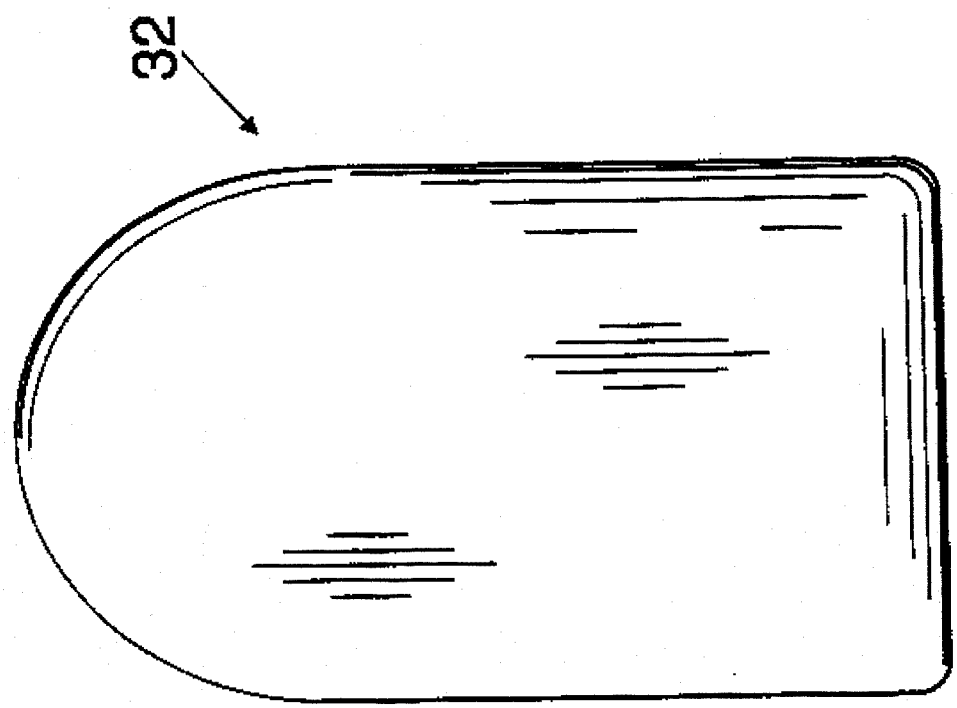

METHOD AND DEVICE FOR CUSHIONING LIMBS

The present application is the United States national application corresponding to International Application No. PCT/US 93/06111 filed Jul. 1, 1993 and designating the United States, which PCT application is in turn a continuation-in-part (CIP) of U.S. application Ser. No. 08/028,925 filed Mar. 4, 1993, now abandoned, which application is in turn a continuation of U.S. application Ser. No. 07/932,422 filed Aug. 19, 1992, now abandoned, which application is in turn a continuation-in-part (CIP) of parent U.S. application Ser. No. 07/909,360 filed Jul. 6, 1992 now abandoned, and of parent U.S. Ser. No. 07/909,361 also filed on Jul. 6, 1992, now abandoned, the benefit of which applications are claimed pursuant to the provisions of 35 U.S.C. §§ 120, 363 and 365 (c).

BACKGROUND

Limbs, including legs, knees, shins, ankles, feet, toes, arms, elbows, forearms, wrists, hands and fingers, can incur pain and discomfort from various afflictions, such as accidents, skin eruptions and deformities.

Foot and toe deformities have been noted from childhood to adolescence and throughout adulthood. Such deformities include bunions, hammertoes, and mallet toes, all of which can lead to pain and/or discomfort for the afflicted individual. Conditions which can develop secondary to these are corns, calluses, plantar warts and blisters. These afflictions are equally painful or discomfortable as the prior afflictions.

Corns are a painful hyperkeratosis, found principally over prominent toe joints and between toes. There are two common types of corns: Heloma Durum and Heloma Molle. Heloma Durum (hard corn) is a hyperkeratotic lesion which appears over a bony prominence and may have a deep nucleus. These corns are normally very tender and painful. The Heloma Molle (soft corn) is a hyperkeratotic lesion which is found between the toes. The soft corn results from pressure exerted between adjacent toes and is soft due to moisture between the toes.

A callus may be a difuse or circumscribed area of hyperkeratosis at a site of repeated pressure and friction. In cases where there is a forefoot imbalance the plantar callus may be found where the metatarsal heads are most prominent.

Plantar warts are simple papilomas caused by a virus. Plantar warts differ from calluses and are not necessarily found over bony prominences. They may be sharply circumscribed with their edges clearly demarcated from the surrounding skin. Their center is darker than the surrounding skin and their may have a mosine appearance. Warts are usually painful to squeezing and often exhibit pain from the pressure of walking.

Hammertoe is a fixed flexion deformity of the proximal interphalangeal joint. This condition is most commonly found in the lesser toes. Other toe deformities include mallet toe which is a flexion deformity of the distal interphalangeal joint.

A blister is a collection of fluid below or within the epidermis caused by excessive frictional forces exerted on the epidermal layer.

Hallux abducto valgus (bunion) is a condition which is characterized by enlargement of the big toe joint and migration of the toe towards the midline of the foot. Heredity is a strong influence in the development of bunions. Bunion deformities are aggravated by improper shoes and a biomechanical imbalance in the rear portion of the foot. A soft tissue bursae may develop over the prominence of the bunion deformity. Bunions typically cannot be cured by using a footcare device; however, the symptoms can be relieved. In some cases, the bunion may be treated with corrective surgery. Pressure and friction over the bunion may cause symptoms such as swelling, inflammation, and development of hyperkeratotic lesions. Bunions secondarily may cause calluses under adjacent metatarsal heads, hammertoes, and corns.

Numerous devices or inserts have been developed to provide cushioning for foot discomfort, including toe-crest pads (i.e. toe-lift pads), heel cushions and heel liners, half-insole or metatarsal pads, full-length and three quarter (¾) length insoles, arch supports, toe caps, toe separators and molded or die-cut sheet cushions for corns, calluses, blisters, bunions and plantar warts. Toe crest pads are typically worn under the toe. Heel cushions are used to treat conditions such as plantar fasciitis, a painful area felt under the heel or calcaneal bursitis (a general pain over the whole calcaneal pad). Heel liners are designed to eliminate shoe slippage, take up room in the shoe and prevent snagging of hose or socks. Half-insoles or metatarsal pads are used for protection in the forefoot region, primarily by women to prevent pain or to prevent the foot from sliding in the shoe. Insoles or innersoles are used for cushioning and shock attenuation, for relief of aching feet and for relief of back pain. Arch supports have been used to relieve foot and leg discomfort caused by flat arches, low arches, high arches, over supination, over-pronation, valgus, varus and other conditions, by realigning the foot to achieve a natural positioning of bone structures. Custom molded shoes, toe caps, felt, moleskin or foam cushions with adhesives, splints, toe separators, or a foam and/or felt devices with toe loops have been used for the treatment of corns, calluses, plantar warts, blisters and bunions.

Most of these devices suffer various disadvantages. For example, bunion devices such as molded plastic splints and rubber shields are generally too large to fit into some shoes and cause discomfort instead of pain relief. Corn, callus, blister, plantar wart and some hammertoe products have the disadvantage of not being reusable after daily use, of lacking the ability to confom to the foot or toe contour, or of inducing maceration of the skin. Devices such as toe crest pads, heel cushions, heel liners, half insoles, metatarsal pads, full length insoles, ¾ length insoles and arch supports typically utilize various cushioning materials in combination with adhesives or adhesive tapes to minimize slippage of the device with footwear. This approach has the disadvantage of requiring completely separate materials (i.e. cushioning and adhesive) to achieve the separate functions of cushioning and attachment to the article of footwear. Further, upon washing, the adhesive used in such devices tends to deteriorate rapidly. Further, most of these materials will induce maceration or softening of the skin.

Organopolysiloxane elastomers are taught in U.S. Pat. Nos. 3,445,420; 3,884,866; and 4,162,243. Such known polysiloxane compositions lack the combination of the requisite tack, or hardness, tensile strength, elongation and/or tear strength for the above applications.

Therefore, research was conducted to make a polysiloxane cushioning material which could serve the dual function of providing both attachment of the device to the limb or to an article of footwear and cushioning of the limb, with little or no maceration of the skin.

SUMMARY OF THE INVENTION

The present invention is directed toward a soft, tacky polysiloxane elastomer formed by curing an organopolysiloxane composition comprising:

(i) a vinyl-containing high viscosity organopolysiloxane or a blend of high viscosity vinyl-containing organopolysiloxanes;
(ii) a low viscosity organopolysiloxane and a blend of low viscosity organopolysiloxanes;
(iii) a reinforcing filler;
(iv) a platinum catalyst; and
(v) a hydrogen containing polysiloxane copolymer wherein the molar ratio of hydrogen to vinyl radicals in the total composition is less than 1.2, such that after curing, the degree to which the soft, tacky, reinforced polysiloxane elastomer is partially crosslinked is 30 to 90%;

wherein
the soft, tacky polysiloxane is characterized as having:
a hardness of 5–55 durometer units (Shore 00),
a tackiness of 10–450 grams as determined by a polyken probe tack tester or 0–7.6 cm (0–3 inches) as determined by a rolling ball tack tester and
a tensile strength of 0.14–5.52 mega Pascals (20–800 pounds/square inch),
a minimum elongation of 250–1100 percent and
a tear strength of 0.88–35.2 kN/m (5–200 pound/square inch).

In a more preferred embodiment, the soft, tacky polysiloxane elastomer is characterized as having:
a hardness of 15–45 durometer units (Shore 00), preferably 20–35 units,
a tackiness of 50–250 grams as determined by a polyken probe tack tester or 0–5 cm (0–2 inches), preferably 0–2.5 cm (0–1 inch), as determined by a rolling ball tack tester and
a tensile strength of 0.35–5.52 mega Pascals (50–800 pounds/square inch),
a minimum elongation of 350–800 percent and
a tear strength of 1.22–26.4 kN/m (7–150 pound/square inch).

In another embodiment, the present invention is directed toward a soft, tacky, reinforced polysiloxane elastomer formed by curing an organopolysiloxane composition comprising, based upon 100 parts total composition:

(i) 20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

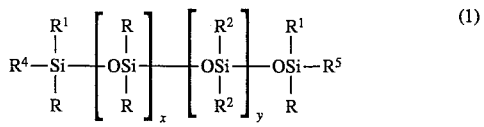

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000, preferably from 50 to 1000; and y varies from 0 to 300, preferably from zero to 50;

(ii) from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

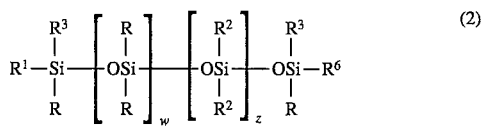

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, preferably from zero to 300, and z varies from 0 to 200, preferably from zero to 50;

(iii) from 15 to 70 parts of a reinforcing filler;
(iv) from 0.1 to 50 parts per million of platinum catalyst (as platinum metal) to the total composition; and
(v) from 0.1 to 50 parts of a hydrogen containing polysiloxane copolymer wherein the molar ratio of hydrogen to alkenyl radicals in the total uncured composition is less than 1.2, such that after curing, the degree to which the soft, tacky, reinforced polysiloxane elastomer is partially crosslinked is 30 to 90%.

In another embodiment, the soft, tacky polysiloxane elastomer is formed into a cushioning device which is sheet padding.

In another embodiment, the soft, tacky polysiloxane elastomer is bonded to a topcover, preferably a topcover which is a polysiloxane elastomer.

The cushioning device containing a topcover can be an arch support pad, a metatarsal pad, a heel cushion, sheet padding, a full-length insole, a three quarter length insole, a half insole, a toe-crest pad, a heel liner, an elbow pad, a knee pad, a shin pad, a forearm pad, a wrist pad, a finger pad, a corn pad, a callus pad, a blister pad, a bunion pad or a toe pad. Limbs which can be protected with the present invention include legs, knees, shins, ankles, feet, toes, arms, elbows, forearms, wrists, hands, fingers or any part thereof. Preferably, the limb padding is reusable after washing.

In another embodiment, the present invention is directed toward a method for cushioning a limb, wherein the limb is a foot or a toe comprising contacting the foot or toe with a cushioning device which is sheet padding, a corn pad, callus pad, blister pad, plantar wart pad, bunion pad or toe pad.

in another embodiment the present invention is directed toward a method for relieving pain or foot discomfort, comprising attaching to an article of footwear the device, which is an arch support pad, a metatarsal pad, a heel cushion, sheet padding, a full-length insole, a three quarter length insole, a half insole, a toe-crest pad or a heel liner.

In another embodiment, the present invention is directed towards limb padding for padding and protecting wrists, ankles, knees, shins, forearms and elbows and a method for protecting such limb parts.

One advantage of the present invention is that it provides a device and a method for relieving limb discomfort, by helping to reduce pressure and friction on the limb.

A second advantage of the present invention is that it provides a footwear insert and a method which are extremely easy to use for relieving foot discomfort.

A third advantage of the present invention is that it provides a reusable, breathable (i.e. permeable) device for relieving limb discomfort that causes little or no masceration after extended contact with the skin.

A fourth advantage of the present invention is that it provides a footwear insert for relieving foot discomfort that can be attached to an article of footwear without the need for further means of attachment, such as by loops, straps, Velcro® fasteners or adhesive coatings or tapes.

A fifth advantage of the present invention is that it provides a device for relieving limb discomfort that can be economically produced using injection molding or extrusion technologies.

A sixth advantage of the present invention is that it provides a footwear insert for relieving foot discomfort in which a single material (i.e. the tacky, cushioning layer) can be used for both attachment to the article of footwear (i.e. tackiness) and for cushioning of the foot, thus simplifying the design of the footwear insert by reducing the number of requisite layers.

A seventh advantage of the device of the present invention is that it retains its tacky properties even after washing and drying.

BRIEF DESCRIPTION OF THE DRAWINGS

FIG. 1 is a perimeter view of arch support pad 26.

FIG. 2 is a cross sectional side view of arch support pad 26.

FIG. 3 is a cross sectional front view of arch support pad 26.

FIG. 4 is a perimeter view of metatarsal pad 28.

FIG. 5 is a cross sectional side view of a metatarsal pad 28.

FIG. 6 is a cross-sectional front view of metatarsal pad 28.

FIG. 7 is a perimeter view of heel cushion 32.

FIG. 8 is a cross-sectional side view of heel cushion 32.

FIG. 9 is a cross-sectional side view of sheet padding 20.

DETAILED DESCRIPTION OF THE INVENTION

Figure 10:
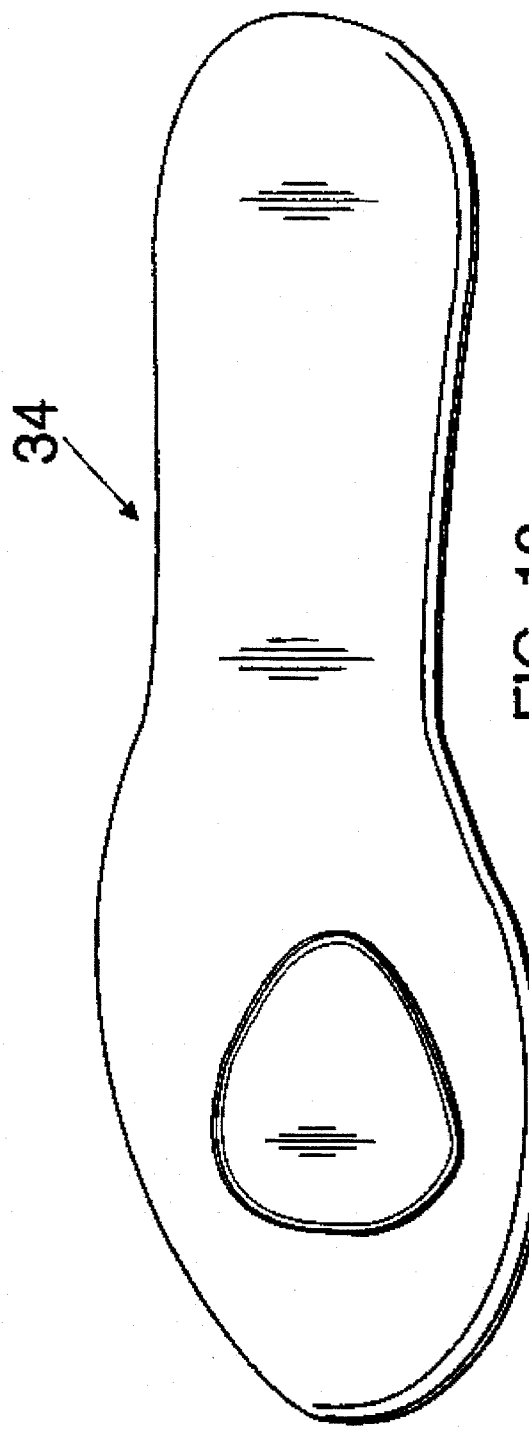
FIG. 10 is a perimeter view of full-length insole 34.
Figure 11:
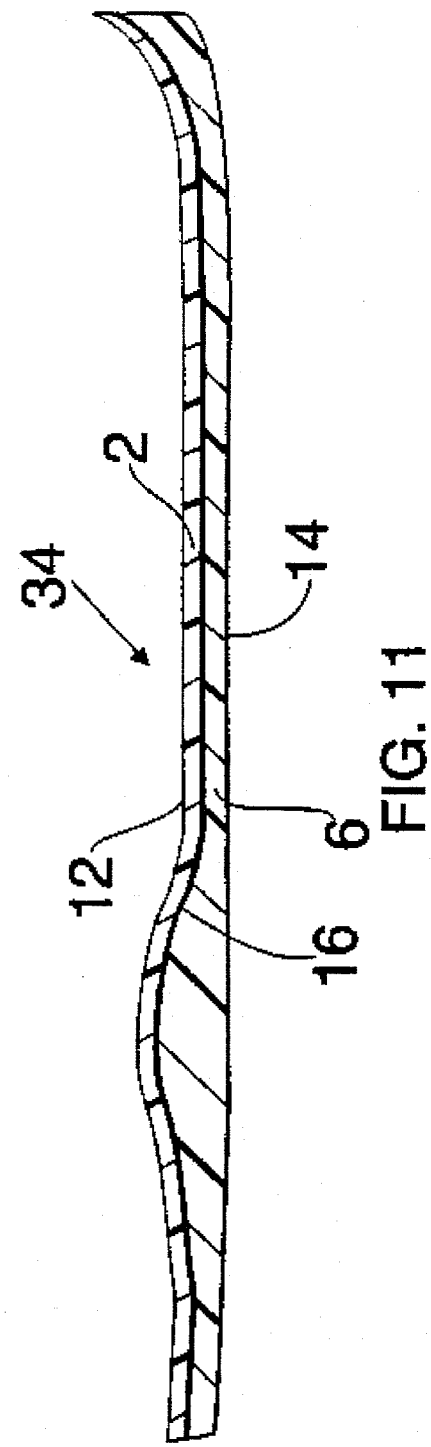
FIG. 11 is a cross sectional side view of full-length insole 34.
Figure 14:
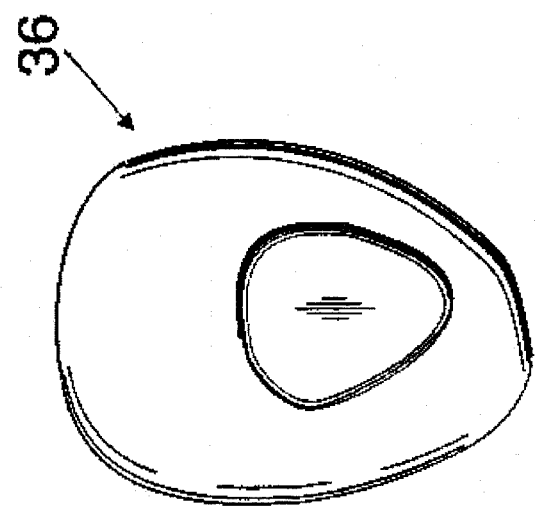
FIG. 14 is a perimeter view of half insole 36.
Figure 15:
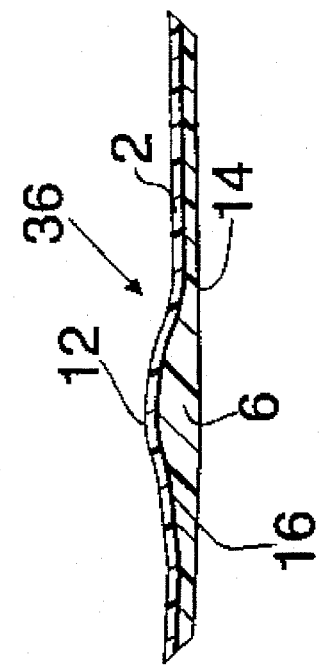
FIG. 15 is a cross-sectional side view of half insole 36.
Figure 12:
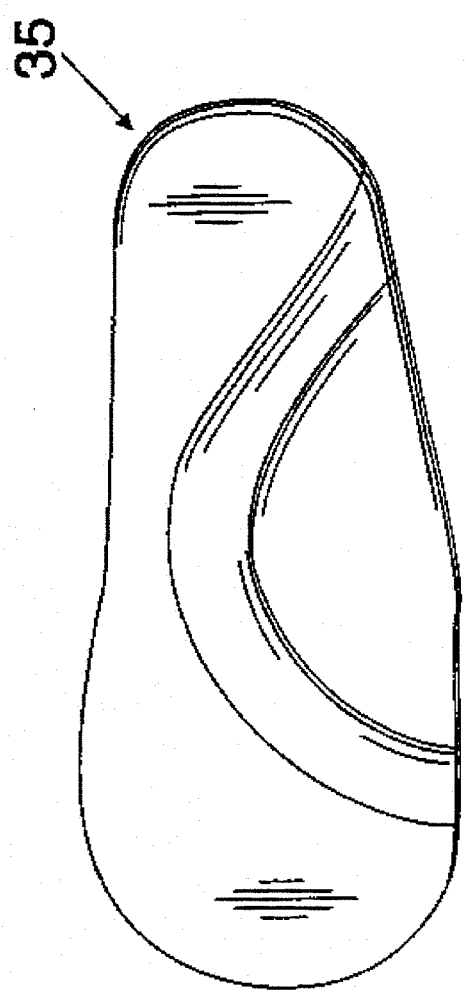
FIG. 12 is a perimeter view of three-quarter length insole 35.
Figure 13:
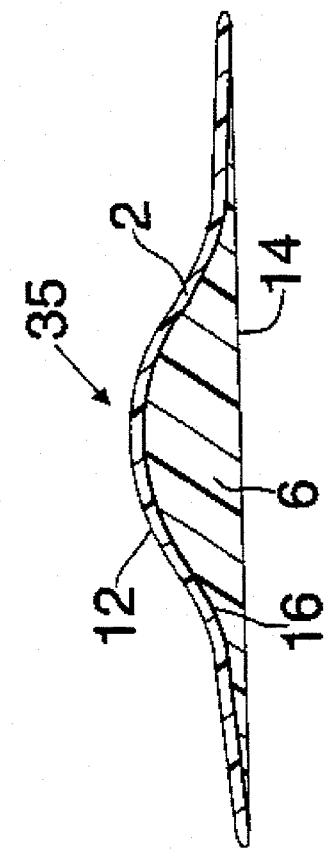
FIG. 13 is a cross sectional side view of three quarter insole 35.
Figure 18:
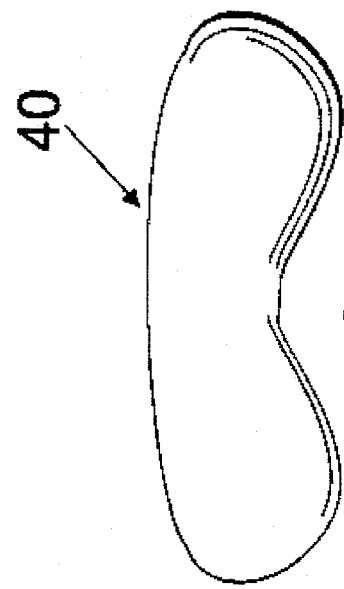
FIG. 18 is a perimeter view of heel liner 40.
Figure 19:
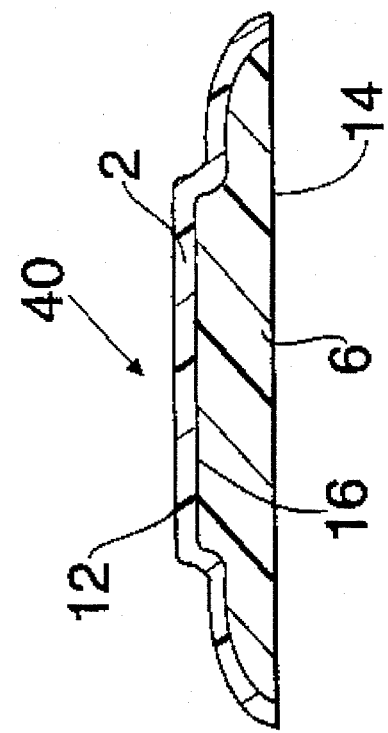
FIG. 19 is a cross sectional side view of heel liner 40.
Figure 16:
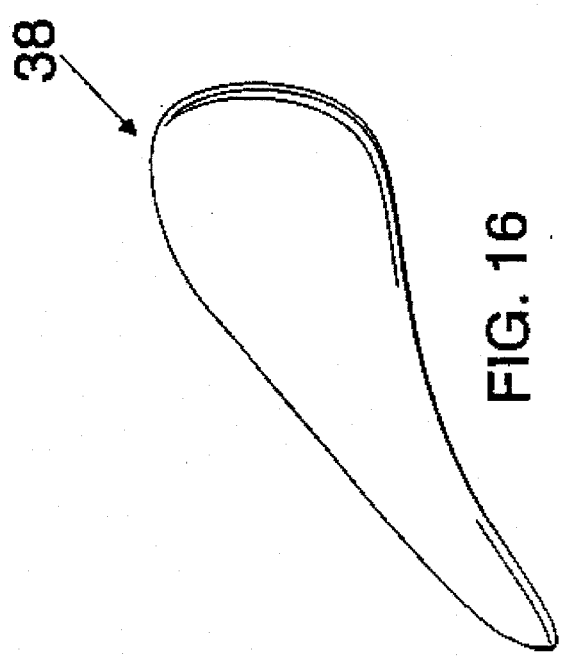
FIG. 16 is a perimeter view of toe crest pad 38.
Figure 17:
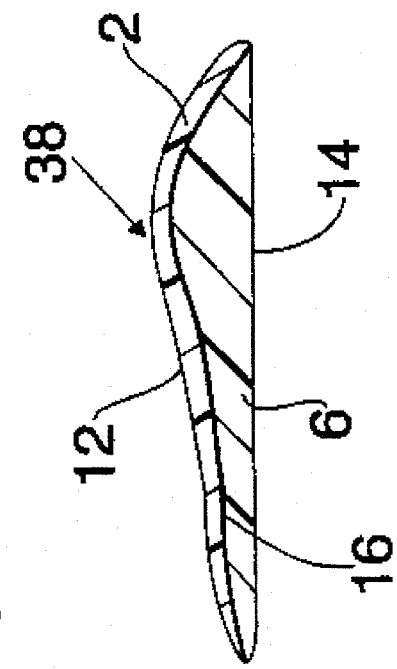
FIG. 17 is a cross sectional front view of toe crest pad 38.
Figure 23:
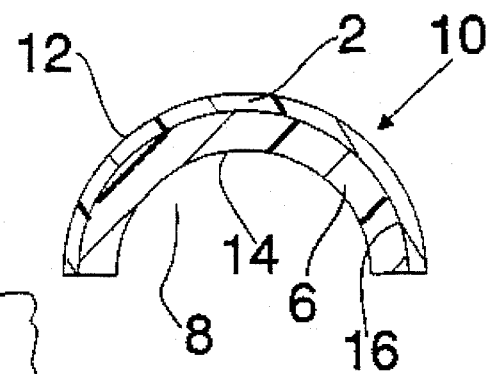
FIG. 23 is a cross sectional front view of cup-shaped pad 10.
Figure 24:
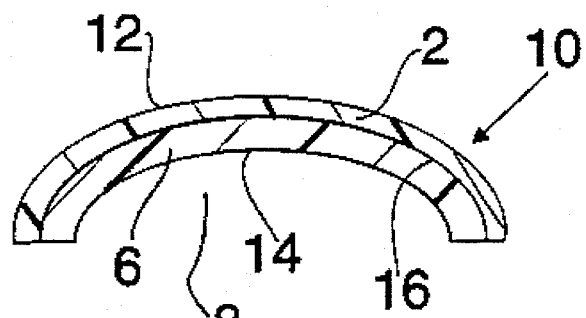
FIG. 24 is a cross sectional side view of cup-shaped pad 10.
Figure 22:
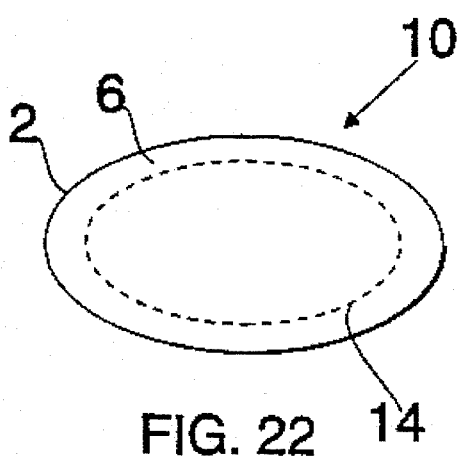
FIG. 22 is a perimeter view for cup-shaped pad 10.
Figure 25:
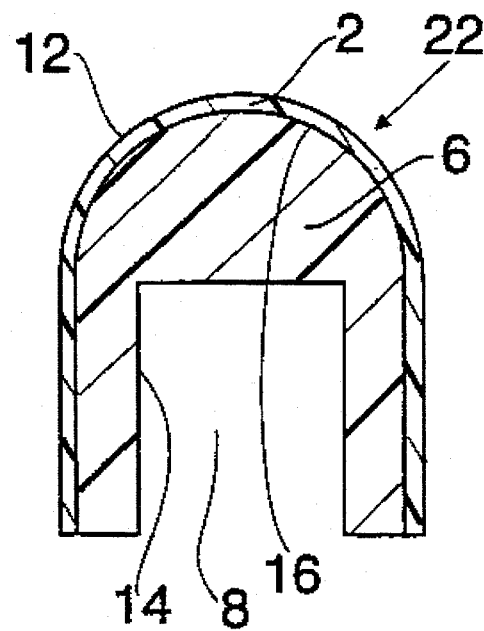
FIG. 25 is a cross sectional view of cylindrically-shaped pad 22.

Refering to the drawings, arch support pad 26 of FIGS. 1,2 and 3; metatarsal pad 28 of FIGS. 4, 5 and 6; heel cushion 32 of FIGS. 7 and 8; sheet padding 20 of FIG. 9; full-length insole 34 of FIGS. 10 and 11; three-quarter length insole 35 of FIGS. 12 and 13; half insole 36 of FIGS. 14 and 15; crest pad 38 of FIGS. 16 and 17; heel liner 40 of FIGS. 18 and 19; cup-shaped pad 10 of FIGS. 22–24 and cylindrically-shaped pad 22 of FIG. 25 share the following common characteristics: they are comprised of topcover 2 and tacky, cushioning layer 6. Topcover 2 typically has a smooth exterior surface 12 and an interior surface 16. The soft, tacky polysiloxane elastomer is described as tacky, cushioning layer 6. Tacky, cushioning layer 6 is bonded to interior surface 16 of topcover 2. Tacky, cushioning layer 6 can be of either uniform or non-uniform thickness, with an exposed surface 14 for attachment to either a limb or to an article of footwear. Where designed for the foot, the device can be shaped to accomodate the toe, metarsal head, heel, arch or insole portion.

FIG. 9 shows sheet padding 20 in which cushioning layer 6 is of substantially uniform thickness and has a exposed surface 14 for attachment to a limb or to an article of footwear. Optionally, sheet padding 20 could be made of tacky, cushioning layer 6, but without topcover 2. One of ordinary skill in the art will appreciate that sheet padding 20 can be cut to form any of the devices of FIGS. 1, 4, 7, 10, 12, 14, 16 and 18.

Figure 20:
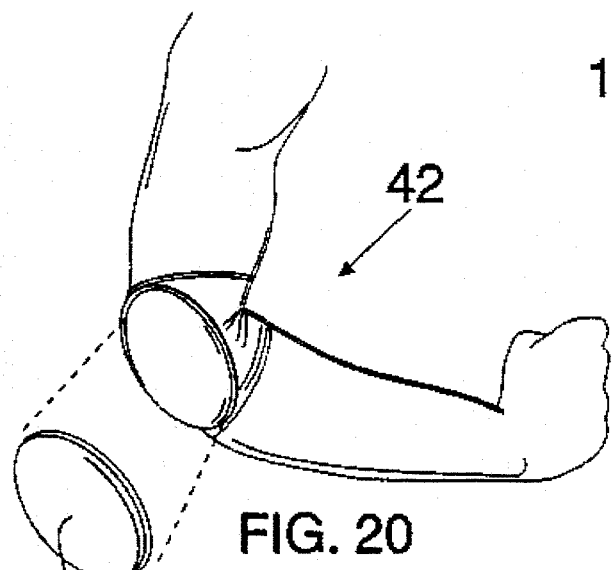
FIG. 20 is limb padding 42 on an arm.
Figure 21:
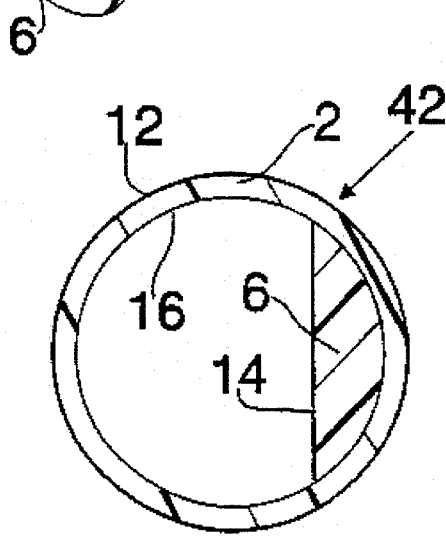
FIG. 21 is a cross-sectional view of limb padding 42.

FIG. 20 shows limb padding 42 attached to the elbow of an arm, in which tacky cushioning layer 6 within padding 42 contacts the elbow for cushioning or protecting the elbow. FIG. 21 shows limb padding 42 having tubular topcover 2 and a tacky cushioning layer 6, wherein tacky, cushioning layer 6 is bonded to the interior 16 of said tubular topcover 2. Tubular topcover 2 can have elastic-type properties for convenient attachment to and holding of the limb padding against limbs, such as shins, ankles, forearms, elbows, knees, hands, fingers and the like. The tubular padding may further comprise supplemental means of attachment, such as loops, straps, Velcro® fasteners and even the tubular topcover. Tacky, cushioning layer 6 is of non-uniform thickness and has a exposed surface 14 for attachment to the elbow, thus preventing slippage of limb padding 42 on the arm.

FIG. 22 shows the perimeter for cup-shaped pad 10. The dash line 14 represents the edge of interior tacky, cushioning layer 6 of pad 10.

In FIGS. 22–25, hollow interior 8 of cup-shaped or cylindrical pad 10 or 22 is designed to receive the limb, i.e. foot, toe or finger, to be contacted with exposed tacky surface 14 of tacky, cushioning layer 6.

In FIG. 25 is shown a cylindrically shaped pad 22 which can be used as a cap for cushioning fingers or toes.

The term "alkyl" refers to radicals having from 1 to 8 carbon atoms per alkyl group, such as methyl, ethyl, propyl, butyl, pentyl, hexyl, octyl and the like.

The term "alkenyl" refers to radicals having from 2 to 8 carbon atoms such as, vinyl, allyl and 1-propenyl.

The term "aryl" refers to mononuclear and binuclear aryl radicals such as, phenyl, tolyl, xylyl, naphthyl and the like; mononuclear aryl alkyl radicals having from zero (i.e. no alkyl group or a bond) to 8 carbon atoms per alkyl group such as benzyl, phenyl and the like.

The term "monovalent hydrocarbon radicals" includes hydrocarbon radicals such as alkyl, alkenyl and aryl.

The term "device" includes devices which are applied either to the limb or to an article of footwear.

The term "tacky" means that the tacky, cushioning layer has an adhesive property that is somewhat sticky to the touch, enabling the pad or sheet padding to be readily attached to the limb, yet is easily removed, i.e. is releasibly attached. It should be recognized that tacky, cushioning layer possesses the requisite tack property throughout the entire cushioning layer (i.e. the interior). However, surface tack can be modified to be greater than or less than the interior tack. Quantitative measurements of tackiness can also be made using a suitable tack tester, such as a Polyken® probe tack tester, a rolling ball tack tester, a peel tester or combinations therof. Tack can be tested with the Polyken® probe tester in accordance with any suitable procedure, such as American Society For Testing and Materials (ASTM) Designation: D2979-71 (Reapproved 1982), Standard Test Method for Pressure-Sensitive Tack of Adhesives Using an Inverted Probe Machine, pp. 187–189, from the Annual Book of ASTM Standards, Vol. 15.09. The Polyken® probe tack tester is the trademark of the Kendall Company, under license by Testing Machines Inc., Mineola, Long Island, N.Y. Tack can also be tested with a rolling ball tack tester in accordance with Pressure Sensitive Tape Council, Test Methods for Pressure Sensitive Tapes, 9th Edition, PSTC-6, revised August, 1989, pp. 29–30 or ASTM D3121. Tack can also be tested with a peel tester in accordance with Pressure Sensitive Tape Council, Test Methods for Pressure Sensitive Tapes, 9th Edition, PSTC-1, revised August 1989, pp. 21–22. The tacky, cushioning layer can be artificially aged prior to tack testing using conventional accelerating aging procedures, such as by exposing the layer to ultraviolet light, elevated temperatures and/or elevated humidity.

The term "macerating" means to soften the skin over a period of time, especially as a result of the skin being wetted or occluded. The tacky cushioning layer of the present invention has little or no ability to induce maceration of the skin, due in part, to its permeability for transporting water vapor from the skin through the tacky, cushioning layer. Thus, the tacky layer of the present invention can provide a third, tri-function of inducing little or no maceration when applied to the skin for an extended period. One test method for evaluating water vapor transmission is ASTM Designation:E96-80, Standard Test Methods for Water Vapor Transmission of Materials, edited May 1987, pp. 629–633.

The term "limb" refers to the paired appendages of the body used especially for movement or grasping, including the legs, knees, shins, ankles, feet, toes, arms, elbows, forearms, wrists, hands, fingers or any part thereof.

The term "cushioning" means that the tacky, cushioning layer protects the limb against forces or shocks.

The term "reusable" means that the device of the present invention can be washed and still retain its property of being easily attached and removed from a limb. We have shown that the washing of residue from a tacky, cushioning layer with subsequent air drying, allows for the regeneration of the tacky surface, enabling reaffixation or attachment of the device to a limb or to an article of footwear. The device can be cleaned using conventional cleansers such as soap and water or alcohols such as isopropanol.

The term "curing" refers to any process by which the raw or uncured polysiloxanes containing reinforcing agents are convened to a finished product, i.e. the soft, tacky, reinforced polysiloxane elastomer. Such curing can be achieved by increasing the molecular weight of the uncured polysiloxane elastomers to the extent desired through crosslinking, using heating or standing at ambient, as described U.S. Pat. No. 3,445,420. Generally, the degree to which the uncured polysiloxane composition can be partially crosslinked can range from about 30 to about 90%, based upon the alkenyl-containing polysiloxane, more preferably from about 30 to about 60%.

The device or sheet padding can be prepared by bonding a layer of the tacky, reinforced polysiloxane elastomer onto a topcover or elastomer sheet using techniques such as compression molding, liquid injection molding, transfer molding, casting and the like.

The topcover of the device and the elastomeric sheet of the sheet padding can be made of high tear strength silicone elastomers such as taught in U.S. Pat. Nos. 3,445,420 and 4,162,243. Other suitable topcover and elastomeric sheet materials can include silicone films, polymeric coatings such as silicone dispersed in xylene such as in U.S. Pat. No. 3,884,866, coated textile materials or other compatible polymers such as polyurethane or polyvinyl chloride (pvc) films. The topcover can be a single material or laminates of several materials.

The tacky, cushioning layer (the cured, tacky reinforced polysiloxane elastomer) may be formed by curing a mixture of a lower alkenyl-functional polysiloxane, such as a vinyl containing polysiloxane, and a hydrogen containing polysiloxane copolymer containing active hydrogen groups. In this regard, the term "hydrogen" refers to active hydrogens which are directly bonded to a silicon atom (Si—H), for example, silicon hydrides and hydrogen containing organopolysiloxanes. Such amounts of the hydrogen containing polysiloxane copolymer will be dependent upon factors such as the molar ratio of alkenyl radicals to active hydrogens in uncured composition and the nature of these components, including such variables as polymer chain length, molecular weight and polymer structure. In its examples, U.S. Pat. No. 3,884,866, discloses organopolysiloxane elastomers having a ratio of hydrogen to vinyl of about 2:1. These elastomers lack the essential property or degree of tackiness necessary to attach a device or sheet padding to the limb and are significantly harder than the organopolysiloxane elastomers employed in the present invention. The organopolysiloxane elastomers employed in the present invention, prior to curing, have a ratio of hydrogens to alkenyl radicals of less than 1.5, preferably 0.5 to 1.2, which imparts the essential property of tack or tackiness. This tackiness is believed to be caused by the partially crosslinked organopolysiloxane elastomers.

Determinations of the hardness of the topcover and of the tacky, cushioning layer can be made with any suitable durometer for testing hardness. One test method entails resting the edge of a Shore 00 durometer on a material, applying a presser foot to the material without shock and taking the average of three readings. Further details for testing hardness can be found in ASTM Test Method D2240. One of ordinary skill in the art will appreciate that elastomers measured by the Shore 00 durometer scale are softer than those measured by the Shore A durometer scale. The elastomers employed in the present invention are signicantly softer than those taught in U.S. Pat. No. 3,844,866.

Representative vinyl-containing high viscosity organopolysiloxanes of formula (1) suitable for preparing a base material include, but are not limited to the following.

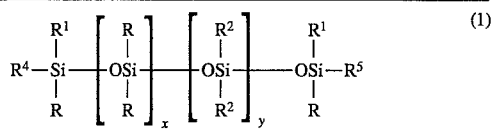

(1)

| Polymer | R | $R^1$ | $R^2$ | $R^4$ | $R^5$ | x | y |
|---|---|---|---|---|---|---|---|
| 1 | $-CH_3$ | $-CH_3$ | $-C_6H_5$ | $-CH_3$ | $-C_2H_3$ | 925 | 50 |
| 2 | $-CH_3$ | $-CH_3$ | $-C_6H_5$ | $-C_2H_3$ | $-C_2H_3$ | 809 | 45 |

-continued

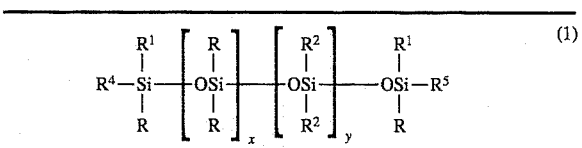

| Pol-ymer | R | R¹ | R² | R⁴ | R⁵ | x | y |
|---|---|---|---|---|---|---|---|
| 3 | —CH₃ | —CH₃ | —C₆H₅ | —C₂H₃ | —C₂H₃ | 611 | 41 |
| 4 | —CH₃ | —CH₃ | —C₆H₅ | —C₂H₃ | —C₂H₅ | 471 | 30 |
| 5 | —CH₃ | —CH₃ | —CH₃ | —C₂H₃ | —CH₃ | 600 | 20 |
| 6 | —CH₃ | —CH₃ | —CH₃ | —C₂H₃ | —C₂H₅ | 800 | 40 |

Representive low viscosity organopolysiloxanes of formula (2) suitable for use in preparing a base material include, but are not limited to the following.

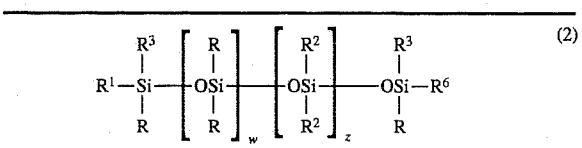

| Pol-ymer | R | R¹ | R² | R³ | R⁶ | w | z |
|---|---|---|---|---|---|---|---|
| 1 | —CH₃ | —C₂H₃ | —C₆H₅ | —CH₃ | —CH₃ | 138 | 13 |
| 2 | —CH₃ | —C₂H₃ | —C₆H₅ | —CH₃ | —CH₃ | 192 | 39 |
| 3 | —CH₃ | —C₂H₃ | —CH₃ | —CH₃ | —CH₃ | 125 | 25 |
| 4 | —CH₃ | —C₂H₃ | —CH₃ | —CH₃ | —CH₃ | 90 | 20 |
| 5 | —CH₃ | —CH₃ | —CH₃ | —CH₃ | —CH₃ | 125 | 25 |

The base material prepared from the vinyl-containing high viscosity organopolysiloxanes of formula (1) and the low viscosity organopolysiloxanes of formula (2) can be admixed with a copolymer containing dimethyl and methyl hydrogen siloxanes. The amount of hydrogen-containing organopolysiloxane used should be sufficient to achieve a ratio of alkenyl radicals to hydrogen in the uncured composition of less than 1.2.

The ratio of the thicknesses of the tacky, cushioning layer to the topcover or the sheet elastomer can range from about 1:1 to about 100:1, preferably about 5 to 60:1; more preferably about 10 to 30:1.

The elastomers are reinforced with a suitable reinforcing agent or filler such as titanium dioxide, calcium carbonate, lithopone, zinc oxide, zirconium silicate, silica aerogel, iron oxide, diatomaceous earth, silazane-treated silica, precipitated silica, fumed silica, mined silica, glass fibers, magnesium oxide, chromic oxide, zirconium oxide, aluminum oxide, alpha quartz, calcined clay and the like, as well as various reinforcing silica fillers taught in U.S. Pat. No. 3,635,743 or mixtures of any of the above, preferably silazane treated silica, precipitated silica and fumed silica or mixtures thereof. Preferably the reinforcing filler is a highly reinforcing silica filler with a surface area ranging from about 80 to about 400 square meters/gram (m²/g), preferably from about 200 to about 400 m²/g. Typically the reinforcing agent is mixed with the vinyl-containing high viscosity organopolysiloxane (1) and low viscosity organopolysiloxane (2) prior to addition of the hydrogen containing polysiloxane copolymer. The reinforcing filler can be employed in the uncured composition in an amount ranging from 10 to about 70 parts per 100 parts of the uncured composition, preferably from 15 to about 40 parts, more preferably from about 20 to about 30 parts. In the cured tacky, reinforced cushioning layer, such amounts correspond to about ten to about 70% by weight, preferably from about 15 to about 40%, more preferably from about 20 to about 30%.

Preferably, the durometer or hardness of the polysiloxane elastomers of the present invention can be lowered (i.e. made softer) by incorporating low viscosity polysiloxanes into the uncured composition. Representative low viscosity polysiloxanes include polydimethylsiloxane fluids or vinyl-containing polydimethylsiloxane fluids. The molecular weight average of the plasticizer can range from about 750 to about 30,000. The low viscosity polysiloxanes can be employed in an amount ranging from about zero to about 50% by weight of the uncured composition, preferably from about 10 to about 30%.

The polysiloxane elastomers of the present invention are further distinguished from known polysiloxane compositions. Such known polysiloxane compositions lack the requisite hardness, tensile strength, elongation and/or tear strength characteristic of Applicants' polysiloxane elastomers, as based upon standard elastic materials testing. For example, unreinforced polysiloxane compositions such as those taught in U.S. Pat. Nos. 3,363,973, 3,548,420, 4,019, 209 must be enclosed in an envelope or other supporting means, i.e. foam impregnation, in order to maintain the shape or durability of an article derived from such compositions. Further, U.S. Pat. No. 4,573,216 teaches impact dissipators in which a polysiloxane viscous-like fluid having an exposed surface is not fully enclosed and is also attached to a supporting structure. However, such polysiloxane viscous-like fluids are not viscoelastic and lack measurable hardness, tensile strength, elongation and/or tear strength. In contrast, Applicants' tacky, polysiloxane cushioning layer is viscoelastic and has a measurable hardness, tensile strength, elongation and/or tear strength.

Further, the tacky, reinforced polysiloxanes of the present invention can retain their elastic properties after prolonged action of compressive stresses, a property known as compression set. Compression set is an indicator of durability. According to ASTM Designation: D395-85, Standard Test Methods for Rubber Property-Compression Set, pp. 34–35, the actual stressing service may involve the maintenance of a definite deflection, the constant application of a known force, or the rapidly repeated deformation and recovery resulting from intermittent compressive forces. Though the latter dynamic stressing, like the others, produces compression set, its effects as a whole are simulated more closely by compression flexing or hysteresis tests. Therefore, compression set tests are considered to be mainly applicable to service conditions involving static stresses. Tests are frequently conducted at elevated temperatures. In a first method utilizing static stresses, a test specimen is compressed to a deflection and maintained under this condition for a specified time and at a specified temperature. In a second method utilizing static stresses, a specified force is maintained under this condition for a specified time and at a specified temperature. After application of the specified deflection or specified force the residual deformation of a test specimen is measured 30 minutes after removal from a suitable compression device in which the specimen has been subjected for a definite time to compressive deformation under specified conditions. After measurement of the residual deformation, the compression set as specified in the appropriate method is calculated according to ASTMD395-85 equations.

Table 1 summarizes dimensional characteristics of selected devices of the present invention for various applications.

|  | Corn Pad | Callus Pad or Blister Pad | Bunion or Hammertoe Pad |
|---|---|---|---|
| THICKNESS | | | |
| inches | 0.03–0.5 | 0.03–0.5 | 0.03–0.5 |
| (preferred) | 0.03–0.125 | 0.03–0.125 | 0.03–0.20 |
| centimeter | 0.0762–1.27 | 0.0762–1.27 | 0.0762–1.27 |
| (preferred) | 0.0762–0.3175 | 0.0762–0.318 | 0.0762–0.318 |
| LENGTH | | | |
| inches | 0.25–3 | 0.5–4 | 0.75–4 |
| (preferred) | 0.5–1.5 | 0.5–1.5 | 1.5–3.0 |
| centimeter | 0.635–7.62 | 1.27–10.16 | 1.905–10.2 |
| (preferred) | 1.07–3.81 | 1.905–7.62 | 3.81–7.61 |
| WIDTH | | | |
| inches | 0.25–2.5 | 0.25–4 | 0.5–4.0 |
| (preferred) | 0.5–1.0 | 1.0–2.0 | 1.0–3.0 |
| centimeter | 0.635–6.35 | 0.635–7.62 | 1.905–6.4 |
| (preferred) | 1.27–2.54 | 2.54–5.08 | 2.54–7.62 |
| HEIGHT | | | |
| inches | 0.05–1.5 | 0.05–1.5 | 0.25–1.5 |
| (preferred) | 0.05–0.5 | 0.05–.0.5 | 0.3–0.75 |
| centimeter | 0.127–3.81 | 0.127–3.81 | 0.635–3.8 |
| (preferred) | 0.127–1.27 | 0.127–1.27 | 0.762–1.90 |

TABLE 2 summarizes selected physical properties of components for preparing a cushioning device of the present invention.

| Properties | Topcover (polysiloxane) | Tacky, Cushioning Layer (polysiloxane) |
|---|---|---|
| HARDNESS | | |
| durometer | 20–80 units (Shore A) | 5–55 units (Shore 00) |
| (preferred) | 45–55 | 15–45; 20–35 |
| TENSILE STRENGTH | | |
| lb/sq inch (psi) | 100–2,000 | 20–800 |
| (preferred) | 300–1500 | 50–800 |
| Mega Pascals | 0.69–13.8 | 0.14–5.53 |
| (preferred) | 2.07–10.35 | 0.35–5.53 |
| MINIMUM ELONGATION | | |
| percent | 100–1500 | 250–1100 |
| (preferred) | 300–800 | 350–800 |
| TEAR STRENGTH | | |
| lb/inch | 75–300 | 5–200 |
| (preferred) | 75–200 | 7–150 |
| kN/m | 13.2–52.8 | 0.88–35.2 |
| (preferred) | 13.2–35.2 | 1.22–26.4 |
| POLYKEN PROBE TACK | | |
| grams[1] | not applicable | 10–450 |
| (preferred) | not applicable | 50–250 |
| ROLLING BALL TACK | | |
| inches | not applicable | 0–3 |
| (preferred) | not applicable | 0–2; 0–1 |
| centimeters | not applicable | 0–7.6 |

TABLE 2-continued summarizes selected physical properties of components for preparing a cushioning device of the present invention.

| Properties | Topcover (polysiloxane) | Tacky, Cushioning Layer (polysiloxane) |
|---|---|---|
| (preferred) PEEL TEST | not applicable | 0–5; 0–2.5 |
| (lb/in) | not applicable | 0.02–80 |
| (preferred) | not applicable | 0.05–40 |
| (kN/m) | not applicable | 0.004–14.08 |
| (preferred) COMPRESSSION SET percent | not applicable | 0.009–7.04 |

[1](polyken probe tack tester, dwell time = 20 seconds, speed 5 cm/sec)

EXAMPLE 1

Using a technique known as compression molding, to a mold cavity heated to 300° F. (149° C.) is dispensed one gram (g) of an elastomer mixture under the trade designation of Silastic 599-HC Liquid Silicone Rubber (Dow Corning, Midland, Mich.). This elastomeric mixture is prepared by combining 1:1 part A to part B of a 2-part addition cure silicone elastomer. A first topmold having a core complementary to the cavity is applied to the elastomer mixture, and the elastomer is cured for about one minute to yield a shell (polysiloxane elastomeric topcover). The first topmold is removed, leaving the resultant elastomeric shell in the cavity mold. About 9 g of an uncured, reinforced polysiloxane elastomer are added to the shell.

The uncured, reinforced polysiloxane elastomer is prepared from the following:

i) 61.0 parts of a high viscosity vinyl (Vi) containing organopolysiloxane of the formula

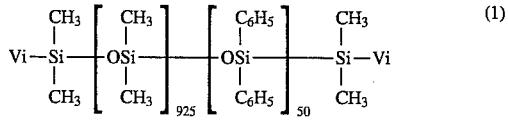

wherein such high viscosity vinyl containing organopolysiloxane (1) has a viscosity of 60,000 centipoise at 25° C.

ii) 15.2 parts of a blend of low viscosity organopolysiloxane (2) which blend has a resulting viscosity of 500 centipoise at 25° C. and in which the organopolysiloxane (2) comprises a mixture of compounds of the following formulas

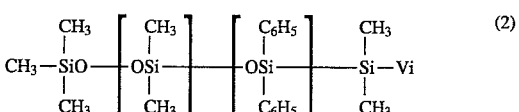

iii) 23.0 parts of silica reinforcing agent treated in the same manner as that disclosed in U.S. Pat. No. 3,635,743 iv) 6 parts per million platinum (0.02% platinum catayst containing 3% platinum metal) of a platinum complex such as that disclosed in U.S. Pat. No. 3,220,972 is added to a premixed base of i–iii)

v) 0.8 parts of a hydrogen-containing polysiloxane of the formula:

$$CH_3-SiO\begin{bmatrix}CH_3\\|\\Si\\|\\CH_3\end{bmatrix}_8\begin{bmatrix}CH_3\\|\\SiO\\|\\H\end{bmatrix}_{10}\begin{matrix}CH_3\\|\\Si-CH_3\\|\\CH_3\end{matrix}$$

wherein the ratio of active hydrogens to vinyl in the uncured composition is about 0.8.

A second topmold having a core slightly smaller than that of the first topmold is applied to the reinforced elastomer to mold or bond the reinforced elastomer onto the elastomeric shell and cured for about two minutes at 137° C. to give a composite pad made of reinforced, soft tacky polysiloxane elastomer bonded to the polysiloxane elastomeric topcover or shell.

Example 2. Using a technique known as compression molding, an unvulcanized silicone sheet is secured to a mold cavity. About 9 g of reinforced elastomer as described in Example 1 are added to the sheet. A topmold having a core slightly smaller than the cavity is applied to the reinforced elastomer to bond the elastomer onto the unvulcanized sheet. The sheet and the elastomer are cured for three minutes to vulcanize the sheet, giving a composite pad having a shell and a tacky, cushioning layer bonded to the shell interior.

EXAMPLE 3

Essentially the same procedure of Example 1 is employed except that the reinforced elastomer is reformulated to 1:1 Component A to Component B.

EXAMPLE 4

Essentially the same procedure of Example 2 is employed except that the reinforced elastomer is reformulated to 1:1 Component A to Component B.

EXAMPLE 5

To a mold cavity heated to 168° F. (75.5° C.) is brushed an uncured dimethyl silicone elastomer dispersion in xylene (Item No. 40000, solids content 35%, available from Applied Silicone Corporation, Ventura, Calif.). The dispersion is allowed to flash for three minutes to begin to form a coating. About 9 g of reinforced elastomer as described in Example 3 are added to the coating in the cavity. A topmold having a core slightly smaller than the cavity is applied to the reinforced elastomer to bond the elastomer onto the coating, and the elastomer and coating are cured for 25 minutes at 350° F. (177° C.) to give the composite pad having a shell and a tacky, cushioning layer bonded to the shell interior.

EXAMPLE 6

Using a technique known as liquid injection molding, a first topmold having a sprue hole (i.e. injection port) is applied to cavity mold complementary to the first topmold, and both molds are heated to a temperature of 270° F. (132° C.). A one gram mixture of the addition cure silicone elastomer of Example 1 (Silastic 599HC liquid silicone rubber) is injected into the mold parts via the sprue hole and cured for about one minute to form an elastomeric shell. The first topmold is removed and the elastomeric shell is removed from the first topmold. The elastomeric shell is placed into a mold cavity heated at 270° F. A second topmold having a sprue hole and a core slightly smaller than the first topmold is placed into the complementary mold cavity containing the shell. About 7.5 g of the reinforced elastomer of Example 3 is injected through the sprue hole into the cavity containing the shell and cured at 270° C. for one minute to give a composite pad.

EXAMPLE 7

Plaques of tacky cushioning layer (3 in.×5 in or 7.6 cm×12.7 cm) are cut into two equal parts. Polyken probe measurements of tackiness are made of the first part using the following standards:
Dwell time: 20 seconds
Speed: 5 cm/sec
To the second part, hand lotion is applied, allowed to stand for two minutes, then washed with soap and water and air dried. A polyken probe tack test is performed on the air dried part. Results indicate that the second part treated with hand lotion and washed had comparable tack values to the untreated first part, indicating that the tacky cushioning layer is reusable after washing.

We claim:

1. A soft, tacky polysiloxane elastomer formed by curing an organopolysiloxane composition comprising:
   (i) a vinyl-containing high viscosity organopolysiloxane or a blend of high viscosity vinyl-containing organopolysiloxanes;
   (ii) a low viscosity organopolysiloxane or a blend of low viscosity organopolysiloxanes;
   (iii) a reinforcing filler;
   (iv) a platinum catalyst; and
   (v) a hydrogen containing polysiloxane copolymer wherein the molar ratio of hydrogen to vinyl radicals in the total composition is less than 1.2, such that after curing, the degree to which the soft, tacky, reinforced polysiloxane elastomer is partially crosslinked is about 30 to about 90%;
   wherein
   the soft, tacky polysiloxane is characterized as having:
   a hardness of 5–55 durometer units (Shore 00),
   a tackiness of 10–450 grams as determined by a polyken probe tack tester or 0–7.6 cm (0–3 inches) as determined by a rolling ball tack tester and a tensile strength of 0.14–5.52 mega Pascals (20–800 pounds/square inch),
   a minimum elongation of 250–1100 percent and
   a tear strength of 0.8–35.2 kN/m (5–200 pound/square inch).

2. The soft, tacky polysiloxane elastomer of claim 1 further characterized as having:
   a hardness of 15–45 durometer units (Shore 00),
   a tackiness of 50–250 grams as determined by a polyken probe tack tester or 0–5 cm (0–2 inches), as determined by a rolling ball tack tester,
   a tensile strength of 0.35–5.52 mega Pascals (50–800 pounds/square inch),
   a minimum elongation of 350–800 percent and
   a tear strength of 1.22–26.4 kN/m (7–150 pound/square inch).

3. The polysiloxane elastomer of claim 2 further characterized as having a hardness of 20–35 durometer units (Shore 00).

4. A soft, tacky, reinforced polysiloxane elastomer formed by curing an organopolysiloxane composition comprising, based upon 100 parts total composition:

(i) 20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

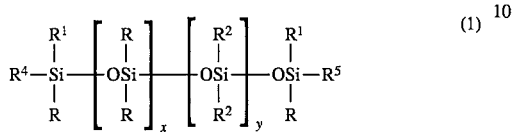
(1)

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000; and y varies from 0 to 300;

(ii) from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

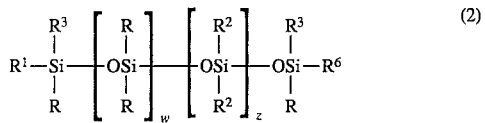
(2)

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, and z varies from 0 to 200;

(iii) from 10 to 70 parts of a reinforcing filler;

(iv) from 0.1 to 50 parts per million of platinum catalyst (as platinum metal) to the total composition; and (v) from 0.1 to 50 parts of a hydrogen containing polysiloxane copolymer wherein the molar ratio of hydrogen to alkenyl radicals in the total uncured composition is less than 1.2, such that after curing, the degree to which the soft, tacky, reinforced polysiloxane elastomer is partially crosslinked is about 30 to about 90%; wherein said soft, tacky reinforced polysiloxane elastomer is further characterized as having:

a hardness of 5–55 durometer units (Shore 00), and a tackiness of 10–450 grams as determined by a polyken probe tack tester or 0–7.6 cm (0–3 inches) as determined by a rolling ball tack tester.

5. The polysiloxane elastomer of claim 4 wherein x varies from 50 to 1000 and y varies from zero to 50.

6. The polysiloxane elastomer of claim 4 wherein w varies from zero to 300 and z varies from zero to 50.

7. The polysiloxane elastomer of claim 4 wherein x varies from 50 to 1000, y varies from zero to 50, w varies from zero to 300 and z varies from zero to 50.

8. The soft, tacky polysiloxane elastomer of claim 4 wherein the ratio of hydrogens to alkenyl radicals in the composition is about 0.5 to 1.2.

9. The soft, tacky polysiloxane elastomer of claim 4 wherein the reinforcing filler is silica.

10. The soft, tacky polysiloxane elastomer of claim 4 wherein the reinforcing filler is silica employed in amounts ranging from about 15 to about 40 parts per 100 parts of the uncured composition.

11. The soft, tacky polysiloxane elastomer of claim 9 wherein the reinforcing silica is silazane treated silica, precipitated silica, fumed silica or mixtures thereof.

12. The soft, tacky, reinforced polysiloxane elastomer according to claim 4 wherein the degree to which the soft, tacky, reinforced polysiloxane elastomer is partially crosslinked is about 30 to about 60%.

13. A cushioning device which is sheet padding made of the soft, tacky polysiloxane elastomer of claim 1.

14. A cushioning device wherein the soft, tacky polysiloxane elastomer of claim 1 is bonded to a topcover.

15. The cushioning device of claim 14 wherein the topcover is a polysiloxane elastomer.

16. The cushioning device of claim 14 which is an arch support pad, a metatarsal pad, a heel cushion, sheet padding, a full-length insole, a three quarter length insole, a half insole, a toe-crest pad, a heel liner, an elbow pad, a knee pad, a shin pad, a forearm pad, a wrist pad, a finger pad, a corn pad, a callus pad, a blister pad, a bunion pad or a toe pad.

17. The cushioning device of claim 14 which is a corn pad, a callus pad, a blister pad, a bunion pad or a corn pad.

18. The cushioning device of claim 14 wherein the device is cup-shaped, the topcover has a convex exterior and a concave interior and the soft, tacky polysiloxane elastomer is bonded to said concave interior of the topcover.

19. A method for cushioning a limb, comprising contacting the limb with the soft, tacky polysiloxane elastomer of claim 1.

* * * * *